US008070320B2

(12) United States Patent
Lee

(10) Patent No.: US 8,070,320 B2
(45) Date of Patent: Dec. 6, 2011

(54) LASER ILLUMINATION DEVICE WITH ADJUSTABLE LIGHT OUTPUT

(75) Inventor: Chia-En Lee, Taipei Hsien (TW)

(73) Assignee: FIH (Hong Kong) Limited, Kowloon (HK)

( * ) Notice: Subject to any disclaimer, the term of this patent is extended or adjusted under 35 U.S.C. 154(b) by 353 days.

(21) Appl. No.: 12/497,747

(22) Filed: Jul. 6, 2009

(65) Prior Publication Data

US 2010/0060968 A1   Mar. 11, 2010

(30) Foreign Application Priority Data

Sep. 11, 2008  (CN) .......................... 2008 1 0304474

(51) Int. Cl.
*G02B 27/20*   (2006.01)

(52) U.S. Cl. ........ 362/259; 362/109; 362/202; 362/277; 362/321; 362/360

(58) Field of Classification Search .................. 362/259, 362/109, 110, 119, 120, 202, 277, 282, 321, 362/322, 360

See application file for complete search history.

(56) References Cited

U.S. PATENT DOCUMENTS

| 2,531,956 | A | * | 11/1950 | Waldorf et al. | 359/673 |
| 3,183,347 | A | * | 5/1965 | Coelho | 362/322 |
| 4,233,650 | A | * | 11/1980 | Hagner et al. | 362/552 |
| 4,425,599 | A | * | 1/1984 | Rieder et al. | 362/552 |
| 4,891,738 | A | * | 1/1990 | Richardson et al. | 362/282 |
| 5,006,965 | A | * | 4/1991 | Jones | 362/552 |
| 5,697,700 | A | * | 12/1997 | Huang | 362/259 |
| 5,788,359 | A | * | 8/1998 | Halsey et al. | 362/118 |
| 5,803,582 | A | * | 9/1998 | Huang | 362/109 |
| 6,024,467 | A | * | 2/2000 | Liu | 362/259 |
| 6,070,992 | A | * | 6/2000 | Schnell | 362/259 |

* cited by examiner

*Primary Examiner* — Ismael Negron
(74) *Attorney, Agent, or Firm* — Altis Law Group, Inc.

(57) ABSTRACT

A laser illumination device including a body, a head secured to the body, a laser generator accommodated in the head, and a rotatable output adjustment member having a graduated disk and an adjustment disk. The graduated disk defines a circle of graduated sections, at least one of which is exposed out of the head. The adjustment disk includes a plurality of through holes with different sizes, arranged in a circle. The measuring member coupled with the graduated disk rotates relative to the body to align each one of the through holes with the laser generator, to adjust the amount of laser light passing through the one of the through holes.

20 Claims, 4 Drawing Sheets

LASER ILLUMINATION DEVICE WITH ADJUSTABLE LIGHT OUTPUT

BACKGROUND

1. Technical Field

The present disclosure relates to laser pens, and particularly to a laser pen used for illuminating workpieces.

2. Description of Related Art

During manufacturing of portable electronic devices, some deficiencies (e.g., stains on shells, flaws in lenses, or scratch marks on display panels) need to be identified and measured. However, these deficiencies are usually too minor to be measured by typical mechanical testing devices.

Therefore, there is room for improvement within the art.

BRIEF DESCRIPTION OF THE DRAWING

Many aspects of the new laser pen can be better understood with reference to the following drawings. The components in the drawings are not necessarily drawn to scale, the emphasis instead being placed upon clearly illustrating the principles of the new laser pen. Moreover, in the drawings, like reference numerals designate corresponding parts throughout the several views.

DETAILED DESCRIPTION

An exemplary laser pen shown in FIGS. 1 through 4 can be implemented for quality testing of portable electronic devices to illuminate flaws e.g., stains on shells, scratch marks on display panels, flaws in lenses, or etc.

Figure 1:
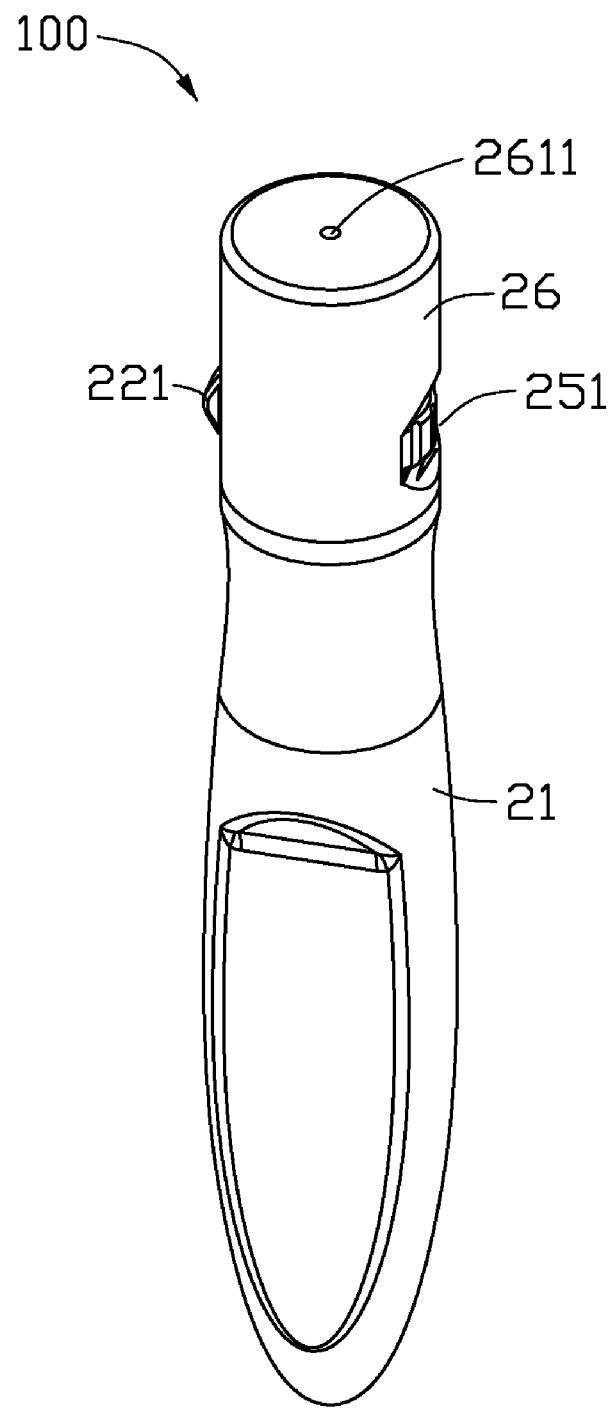
FIG. 1 is an assembled, isometric view of a laser pen according to an exemplary embodiment.
Figure 2:
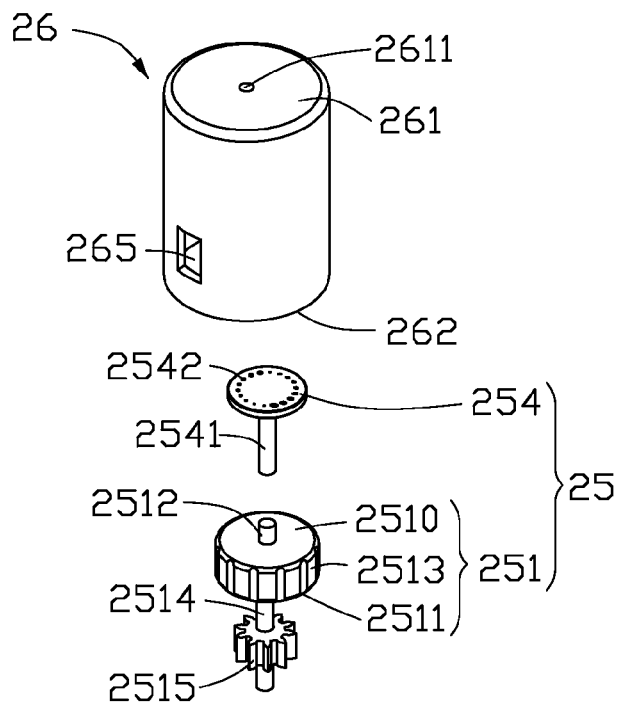
FIG. 2 is an disassembled view of the laser pen shown in FIG. 1.
Figure 2:
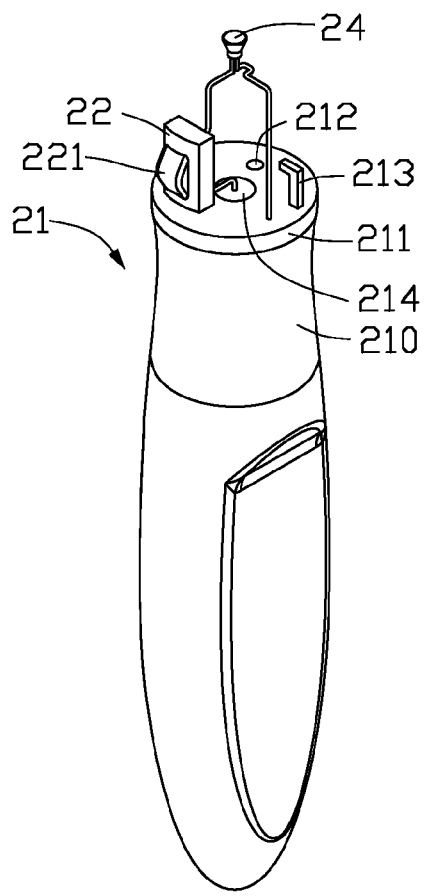

Referring to FIGS. 1 and 2, the laser pen 100 includes a pen body 21, a power switch 22, a laser generator 24, a adjustment member 25, a pen head 26, and a power supply (not shown). The pen head 26 can be secured to an end of the pen body 21.

The pen body 21 includes a body portion 210 and a connecting portion 211. The body portion 210 is generally hollow to receive the power supply therein. The connecting portion 211 connects to an end of the body portion 210. The exterior upper wall of the connecting portion 211 defines a blind hole 212 therein, an elastic mating member 213 protruding therefrom, and an electrically conducting member 214 embedded therein. The elastic mating member 213 is L-shaped and adjacent to the blind hole 212. The electrically conducting member 214 is located at the center of the exterior upper wall and used to electrically connect the power supply.

The power switch 22 is fixed to the connecting portion 211. The power switch 22 includes a switch button 221. The power switch 22 electrically connects to the electrically conducting member 214 and the laser generator 24. The laser generator 24 is coaxial with the electrically conducting member 214 and electrically connects to the power switch 22 and the power supply.

The adjustment member 25 includes a graduated disk 251 and a adjustment disk 254. The graduated disk 251 has an upper surface 2510 and an opposite lower surface 2511. The upper surface 2510 has a cylindrical first connecting post 2512 protruding from the center. The lower surface 2511 has a cylindrical second connecting post 2514 protruding from the center. The first and second connecting posts 2512, 2514 are coaxial. The second connecting post 2514 can rotatably engage into the blind hole 212, so that the graduated disk 251 can rotate relative to the connecting portion 211. The circumferential wall of the adjustment member 25 defines a plurality of continuous graduated sections 2513 around there, and the values for measurement of the graduated sections 2513 directly indicate various amounts of a laser light emitted from the laser generator 24 striking on testing workpiece. The second connecting post 2514 has a gear 2515 fixed thereon. The gear 2515 can matingly engage with the elastic mating member 213 to maintain positions of the rotating graduated disk 251 relative to the pen body 21.

The lower surface of the adjustment disk 254 has a third connecting post 2541 extending to fix with the first connecting post 2512. The adjustment disk 254 defines a circle of through holes 2542 around the center. The diameters of one semi-circle of through holes 2542 increase clockwise, and the other semi-circle of through holes 2542 proximate to the previous through holes 2542 also increase clockwise.

The through holes 2542 correspond to the graduated sections 2513, so that the diameters of the through holes 2542 correspond with the values of the graduated sections 2513. Each of the through holes 2542 may align with the laser generator 24 when the graduated disk 251 coupled with the adjustment disk 254 rotates about the laser generator 24 in a circle. The through holes 2542 allow the laser light emitted from the laser generator 24 to partially pass therethrough.

Figure 3:
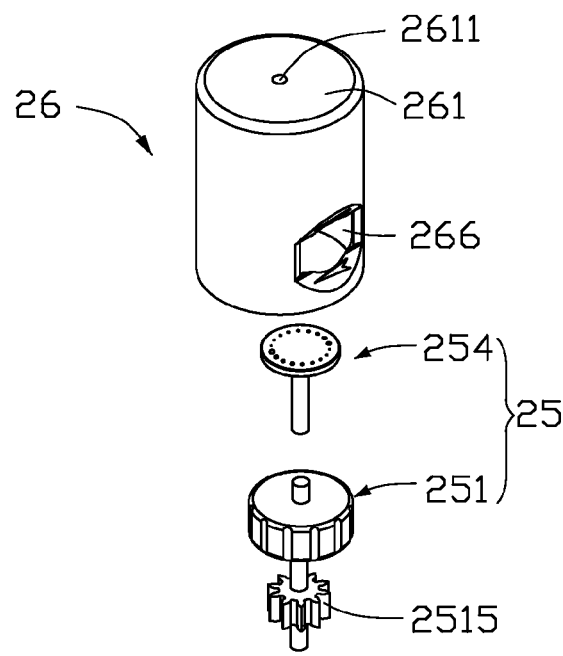
FIG. 3 is similar to FIG. 2, but showing another aspect.
Figure 3:
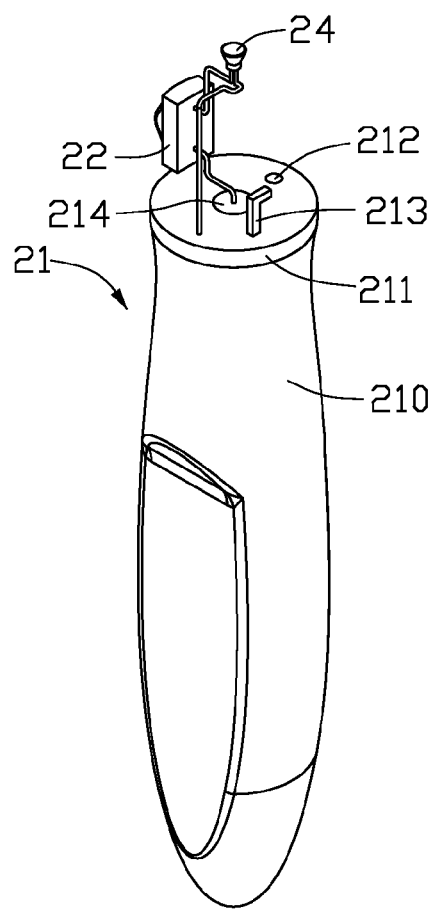
Figure 4:
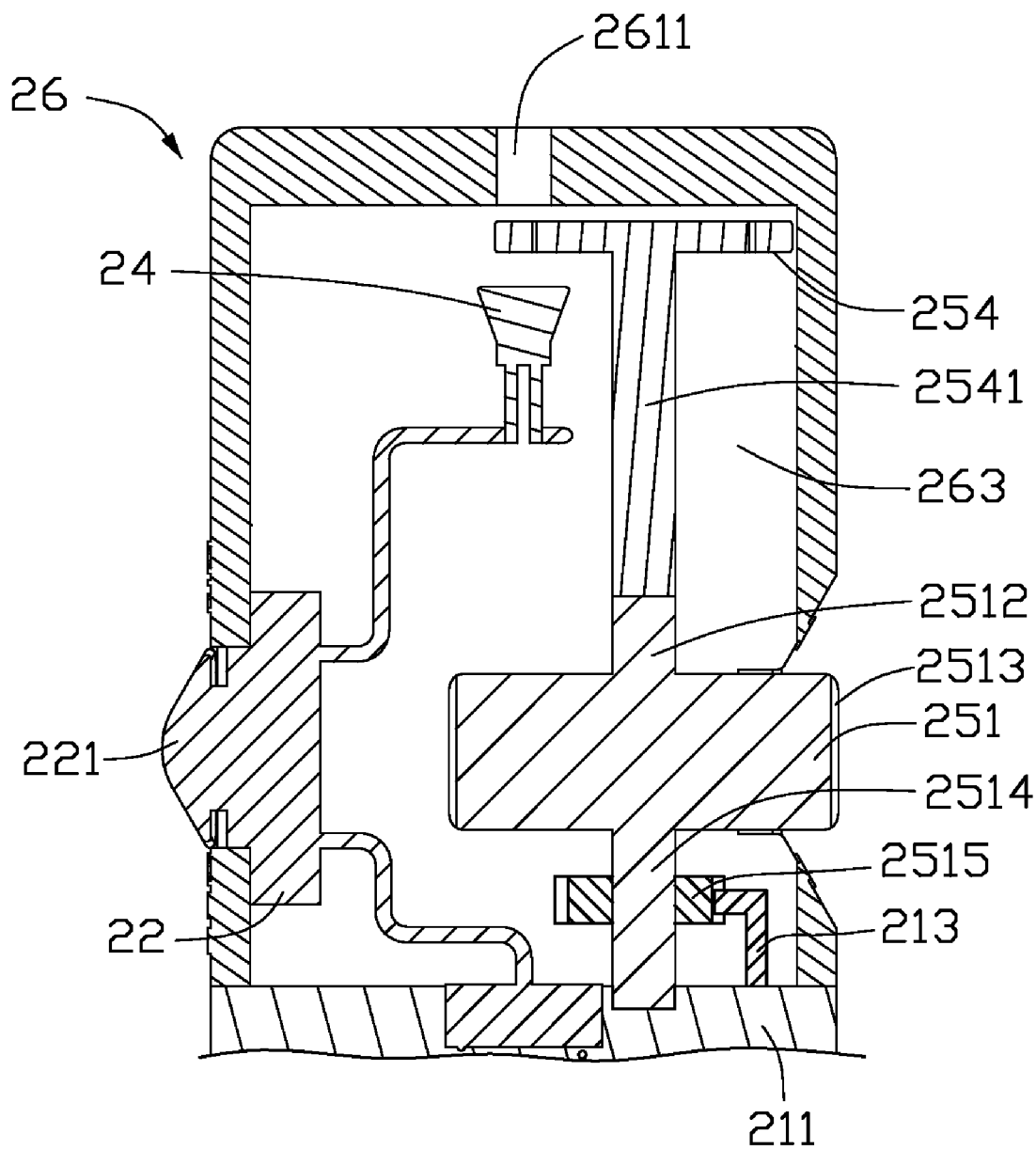
FIG. 4 is a cross-sectional view of the pen laser shown in FIG. 1.

Referring further to FIGS. 3 and 4, the pen head 26 is hollow including a closed end portion 261, an opened end portion 262 opposite to the closed end portion 261. The pen head 26 further defines an accommodating cavity 263 through the opened end portion 262. The closed end portion 261 defines a light hole 2611 in the center to communicate with the accommodating cavity 263. The light hole 2611 is larger than all through holes 2542. The pen head 26 has a switch button hole 265 and a through slot 266 defined through its peripheral wall. The switch button hole 265 and the through slot 266 communicate with the accommodating cavity 263. The switch button hole 265 is used to mount the switch button 221. The through slot 266 is located opposite to the switch button hole 265 for exposing at least one graduated section 2513 of the graduated disk 251 out of the pen head 26.

During assembly, the third connecting post 2541 is fixed to the first connecting post 2512 of the graduated disk 251, integrally connecting the adjustment disk 254 with the graduated disk 251. The adjustment disk 254 is coaxially positioned above the laser generator 24. The second connecting post 2514 can be inserted into the blind hole 212 and the elastic mating member 213 mates with the gear 2515. The pen head 26 can be secured to the pen body 21. At this stage, the power switch 22, the laser generator 24 and the adjustment member 25 are accommodated into the accommodating cavity 263. The switch button 221 is exposed through the switch button hole 265 to the outside. The graduated disk 251 is partially exposed through the through slot 266, so that at least one graduated section 2513 is exposed. The light hole 2611 and the through hole 2542, and the laser generator 24 align with each other.

In use, by pressing the switch button 221, the laser generator 24 is turned on to emit laser light. The graduated disk 251 can be rotated to select a specified graduated section 2513 by manually rotating the exposed graduated section 2513. During this course, the elastic mating member 213 rotatably engages with the gear 2515 and finally secures the position of the graduated disk 251 coupled with the measuring disk 254 relative to the laser generator 24. The laser light penetrates through the through hole 2542 and the light hole 2611 to strike on the testing workpiece to illuminate flaws e.g., scratch marks.

It is to be understood that the amount of the laser light can be adjusted by rotating the graduated disk 251 to select another specified graduated section 2513. In this case, the adjustment disk 254 is rotated to use another through hole 2542 with a different size than the previous through hole 2542 to align with the laser generator 24 and the light hole 2611. The amount of the laser light striking on the testing workpiece is thus adjusted.

It is to be understood, however, that even through numerous characteristics and advantages of the exemplary invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A laser pen, comprising:
    a pen body;
    a pen head secured to the pen body;
    a laser generator accommodated in the pen head, the laser generator configured for emitting a laser light;
    a power switch configured for switching the laser generator on or off; and
    an adjustment member rotatably secured on the pen body and accommodated in the pen head, the adjustment member comprising:
    a graduated disk being rotatable relative to the pen body, the graduated disk defining a circle of graduated sections, at least one of the graduated sections exposed out of the pen head; and
    an adjustment disk coupled with the graduated disk, the adjustment disk defining a circle of through holes corresponding to the graduated sections, each through hole configured for allowing a predetermined amount of the laser light to pass therethrough.

2. The laser pen as claimed in claim 1, wherein the graduated disk comprises a second connecting post formed at the center, the pen body comprises a connecting portion, the connecting portion defines a blind hole, the second connecting post rotatably engages into the blind hole, so that the graduated disk is rotatably relative to the connecting portion.

3. The laser pen as claimed in claim 2, wherein the graduated disk further comprises a first connecting post formed thereon, the adjustment disk comprises a third connecting post formed thereon, the third connecting post fixed to the first connecting post.

4. The laser pen as claimed in claim 3, wherein the circle of graduated sections are defined circumferentially around the graduated disk, the circle of through holes are defined around the center of the adjustment disk.

5. The laser pen as claimed in claim 4, wherein the sizes of the graduated sections directly indicate the amount of the laser light emitted through a corresponding through hole.

6. The laser pen as claimed in claim 3, wherein the connecting portion comprises an elastic member adjacent to the blind hole, the second connecting post comprises a gear fixed thereon, the elastic mating member mating with the gear.

7. The laser pen as claimed in claim 6, wherein the pen body further comprises a body portion, the connecting portion fixed to the body portion, the connecting portion comprises an electrically conducting member embedded therein.

8. The laser pen as claimed in claim 7, wherein the power switch comprises a switch button, the power switch electrically connects with the electrically conducting member, the laser generator configured for co-axially aligning with each of the through holes when the adjustment disk rotates.

9. The laser pen as claimed in claim 7, wherein the pen head comprises a closed end portion and an opened end portion, and defines an accommodating cavity communicating with the opened end portion, the closed end portion defines a light hole through the center thereof, the light hole communicates with the accommodating cavity, and the light hole co-axially aligns with the laser generator and larger than all through holes.

10. The laser pen as claimed in claim 9, wherein the pen head defines a switch button hole and the through slot communicating with the accommodating cavity, the switch button hole accommodating the switch button, the through slot exposing the at least one graduated section out of the pen head.

11. A laser pen for illuminating a workpiece, comprising:
    a pen body;
    a pen head secured to the pen body;
    a laser generator accommodated in the pen head, the laser generator configured for emitting a laser light; and
    an adjustment member accommodated in the pen head, the adjustment member being rotatable relative to the pen body, the adjustment member comprising:
    a graduated disk, the graduated disk defining a circle of graduated sections, at least one of the graduated sections exposed out of the pen head; and
    an adjustment disk, the adjustment disk defining a circle of continuous through holes with different sizes, the adjustment member coupled with the graduated disk configured for being rotated relative to the pen body to align each one of the through holes with the laser generator so as to adjust the amount of laser light passing through the one of the through holes and striking on the workpiece.

12. The laser pen as claimed in claim 11, further comprising a power switch configured for switching the laser generator on or off, the laser generator emitting the laser light.

13. The laser pen as claimed in claim 12, wherein the graduated disk comprises a first connecting post and a second connecting post formed at the center, the first and the second connecting posts are oppositely arranged, the pen body comprises a connecting portion, the connecting portion defines a blind hole, the second connecting post rotatably engages into the blind hole, the adjustment disk comprises a third connecting post formed thereon, and the third connecting post is fixed to the first connecting post.

14. The laser pen as claimed in claim 13, wherein the circle of graduated sections are defined circumferentially around the graduated disk, the circle of through holes are defined around the center of the adjustment disk.

15. The laser pen as claimed in claim 14, wherein the sizes of the graduated sections directly indicate the amount of the laser light emitted through a corresponding through hole.

16. The laser pen as claimed in claim 13, wherein the connecting portion comprises an elastic member adjacent to the blind hole, the second connecting post comprises a gear fixed thereon, the elastic mating member mating with the gear.

17. The laser pen as claimed in claim 16, wherein the pen body further comprises a body portion, the connecting portion fixed to the body portion, the connecting portion comprises an electrically conducting member embedded therein.

18. The laser pen as claimed in claim 17, wherein the power switch comprises a switch button, the power switch electrically connects with the electrically conducting member, the laser generator configured for co-axially aligning with each of the through holes when the adjustment disk rotates.

19. The laser pen as claimed in claim 17, wherein the pen head comprises a closed end portion and an opened end portion, and defines an accommodating cavity communicating with the opened end portion, the closed end portion defines a light hole through the center thereof, the light hole communicates with the accommodating cavity, and the light hole co-axially aligns with the laser generator and larger than all through holes.

20. The laser pen as claimed in claim 19, wherein the pen head defines a switch button hole and the through slot communicating with the accommodating cavity, the switch button hole accommodating the switch button, the through slot exposing the at least one graduated section out of the pen head.

* * * * *